(12) United States Patent
Kirchhofer et al.

(10) Patent No.: US 7,357,791 B2
(45) Date of Patent: *Apr. 15, 2008

(54) DEVICE FOR ADMINISTERING AN INJECTABLE PRODUCT

(75) Inventors: Fritz Kirchhofer, Sumiswald (CH); Jürg Steck, Kirchberg (CH); Peter Hostettler, Ersigen (CH); Stephan Jost, Bollingen (CH); Hanspeter Heiniger, Lotzwil (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/554,308

(22) Filed: Oct. 30, 2006

(65) Prior Publication Data

US 2007/0100292 A1 May 3, 2007

Related U.S. Application Data

(63) Continuation of application No. 09/902,091, filed on Jul. 10, 2001, now Pat. No. 7,128,728, which is a continuation of application No. 09/311,434, filed on May 14, 1999, now Pat. No. 6,258,068.

(30) Foreign Application Priority Data

May 15, 1998 (DE) .................... 198 21 933

(51) Int. Cl.
*A61M 5/00* (2006.01)
*A61M 5/20* (2006.01)

(52) U.S. Cl. ............... 604/208; 604/135; 604/187

(58) Field of Classification Search ........ 604/131–137, 604/152, 187, 192, 208, 218, 232, 264, 272
See application file for complete search history.

(56) References Cited

U.S. PATENT DOCUMENTS

| 4,561,856 A |   | 12/1985 | Cochran |
|---|---|---|---|
| 4,850,967 A | * | 7/1989 | Cosmai ........................ 604/68 |
| 5,080,649 A |   | 1/1992 | Vetter |
| 5,620,421 A |   | 4/1997 | Schmitz |
| 5,658,259 A |   | 8/1997 | Pearson et al. |
| 6,221,046 B1 | * | 4/2001 | Burroughs et al. ......... 604/153 |
| 6,258,068 B1 | * | 7/2001 | Kirchhofer et al. ......... 604/208 |
| 6,793,646 B1 | * | 9/2004 | Giambattista et al. ........ 604/90 |
| 7,128,728 B2 | * | 10/2006 | Kirchhofer et al. ......... 604/135 |

FOREIGN PATENT DOCUMENTS

| DE | 4223958 | 1/1993 |
|---|---|---|
| DE | 3645245 | 1/1994 |
| DE | 4428467 | 2/1996 |
| EP | 0 268 191 A2 | 5/1988 |
| WO | WO 88/10129 | 12/1988 |

* cited by examiner

*Primary Examiner*—Kevin C. Sirmons
*Assistant Examiner*—Bhisma Mehta
(74) *Attorney, Agent, or Firm*—David E. Bruhn; Dorsey & Whitney LLP

(57) ABSTRACT

The invention provides a injection device for administering an injectable product, including a base section adapted to receive a container from which a product dose is dispensed through a needle by displacement of a piston in the container, and a drive unit including a driven member, a drive element and a damping arrangement, the drive unit for applying a force to advance the piston in the container to dispense a dose, wherein the damping arrangement generally counteracts the drive force and counter forces. The invention also encompasses a needle safety sleeve and a blocking structure for use with injection devices.

21 Claims, 7 Drawing Sheets

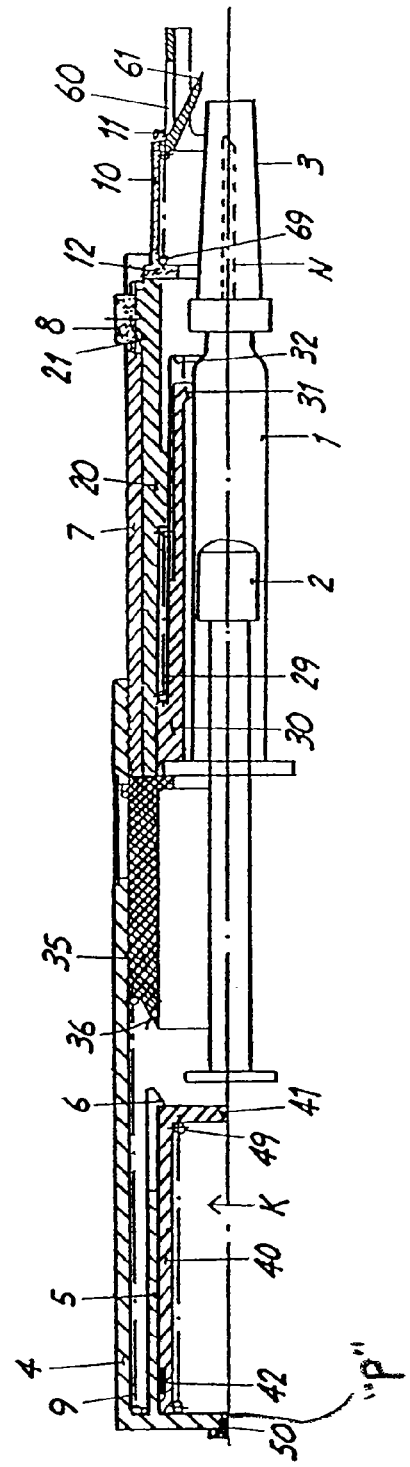
FIG. 1a
FIG. 1
Fig 1b

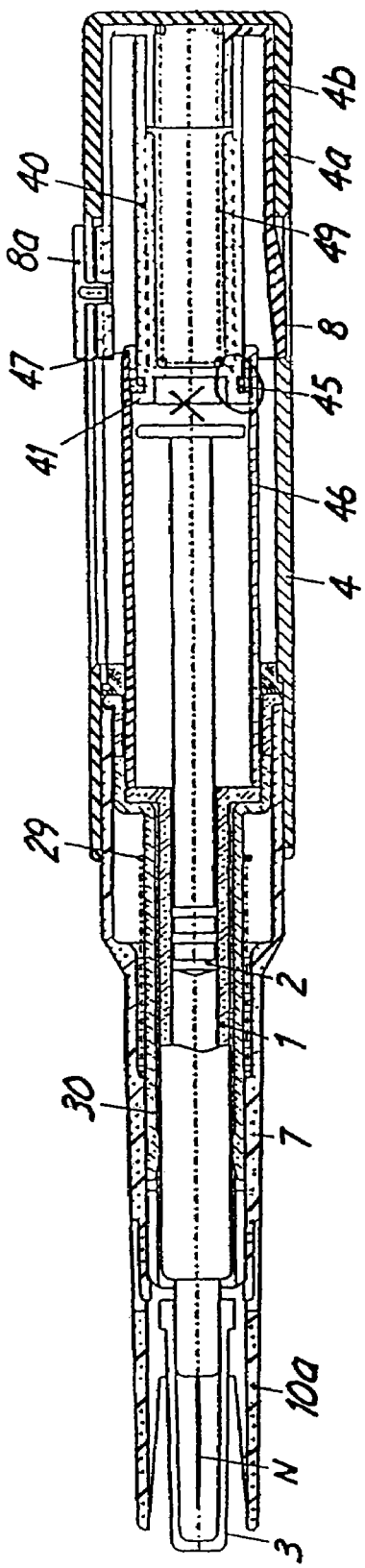
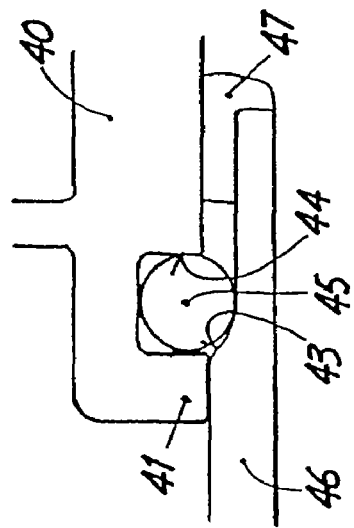
FIG. 3
FIG. 3a

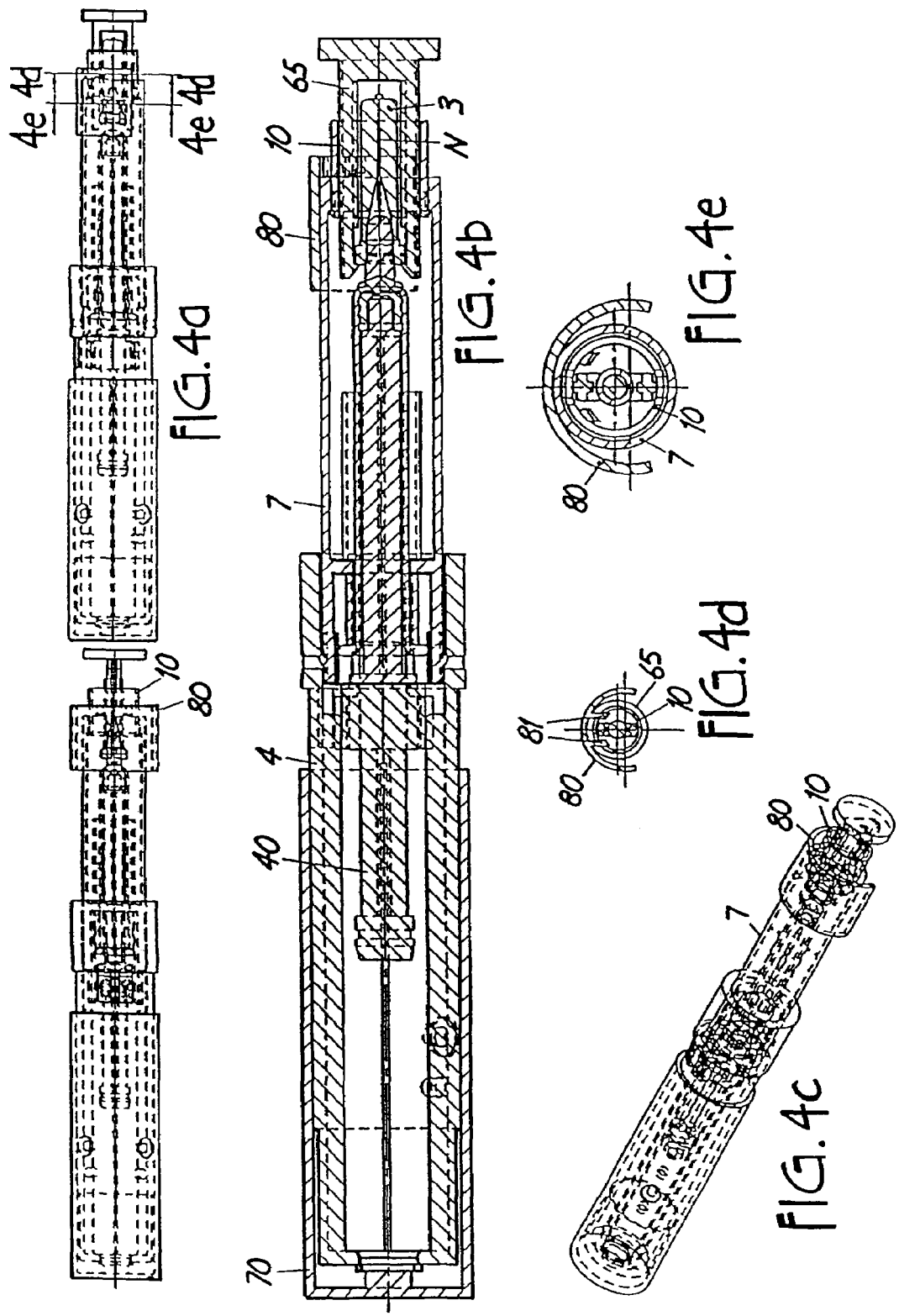

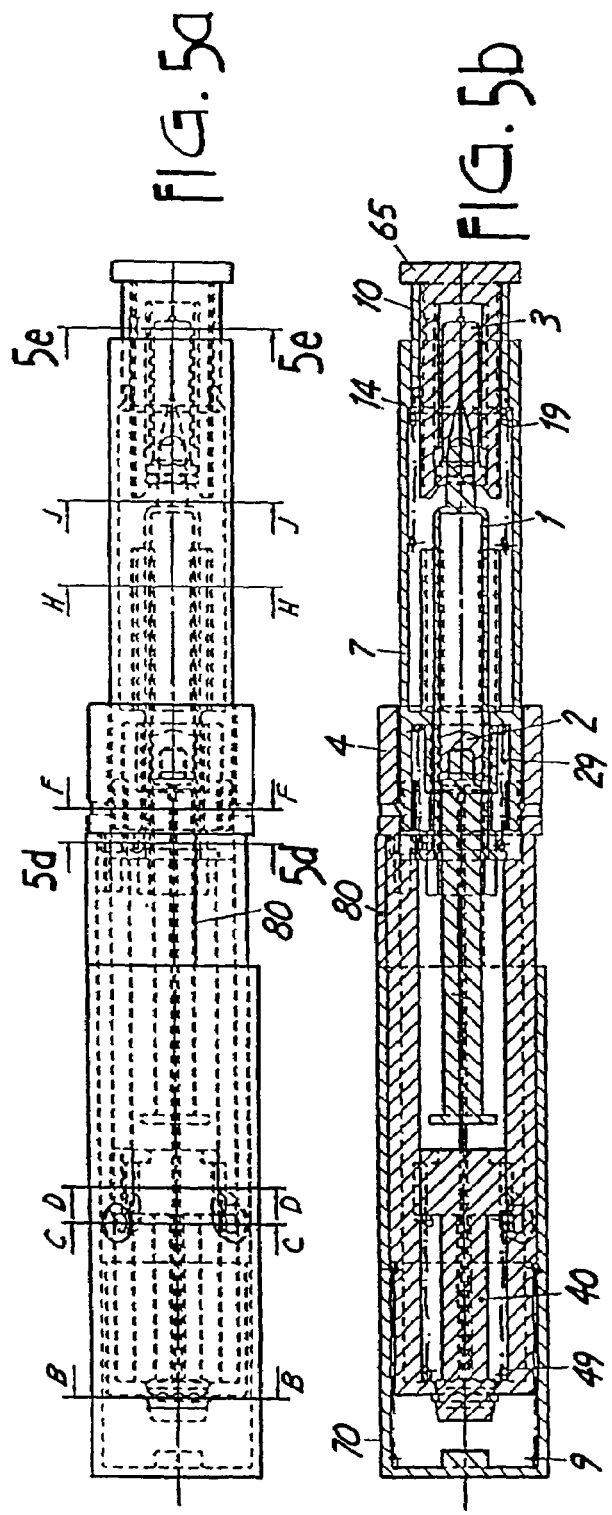

DEVICE FOR ADMINISTERING AN INJECTABLE PRODUCT

RELATED APPLICATIONS

This application is a continuation of U.S. application Ser. No. 09/902,091, filed on Jul. 10, 2001, now issued as U.S. Pat. No. 7,128,728, issued on Oct. 31, 2006, which is a continuation of U.S. application Ser. No. 09/311,434, filed on May 14, 1999, now issued as U.S. Pat. No. 6,258,068, issued on Jul. 10, 2001, which claims priority to German Application No. 198 219 334.4, filed on May 15, 1998, the contents of which are incorporated in their entirety by reference herein.

BACKGROUND

The invention relates to devices for administering injectable products, in particular the injection of medically or cosmetically effective products.

Devices which the invention also concerns are known as injection pens. Generally, an injection pen comprises an elongated, hollow cylindrical housing in which a container, having the shape of an ampoule, filled with the product to be administered, is received. An injection needle is attached to the container and when so attached is generally axially aligned with or parallel to the central longitudinal axis of the housing, extending generally from one end of the housing. A drive unit for a piston within the container is also arranged in the housing. The piston is advanced in forward direction within the container under the effect of a driven member of the drive unit, thus causing a predetermined product dose to be dispensed. For advancing the piston, the driven member itself is advanced in the forward direction (i.e., toward the needle) in relation to the housing, either manually or by the drive force of a drive element of the drive unit. In the latter case, energy is stored in the drive unit, which energy is converted into a drive force driving the driven member forward upon the drive unit being actuated.

In the course of advancement of the driven member, the stored energy or at least part of the same is consumed. The drive force exerted by the drive element on the driven member is consequently reduced while the driven member is being advanced. Typically towards the end of the injection or dispensing cycle, the advancing or forward speed of the driven member decreases and, therefore, the dispensing rate will decrease, i.e., dispensing is not uniformly distributed over the total injection or dispensing cycle. Other interferences or counter forces may be caused by irregularities in the internal diameter of the ampoule, resulting in the wall frictional forces affecting the piston, causing non-constant piston movement over the stroke of the piston and making uniform dispensing or injection difficult.

SUMMARY

It is an object of the invention to provide for the uniform dispensing or injecting of an injectable product in devices for administering such products.

In one embodiment, the invention is an injection device comprising a base section and a drive unit including a driven member, a drive element and a damping arrangement. Typically, the base section may accommodate a container from which a product dose is dispensed through a needle by displacement of a piston in the container. The drive unit applies a force to advance the piston in the container to dispense a dose, and the damping arrangement is adapted to generally counteract the drive force and other counter forces produced during use of the device.

In another embodiment according to the invention, a device for administering an injectable product comprises a base section, a container arranged in or on the base section, from which container a product is dispensed through a needle by displacement, in a forward direction, of a piston being arranged in the container, and a drive unit comprising a driven member and a drive element, wherein the drive element exerts a drive force on the driven member upon the drive unit being actuated, thus displacing the driven member in the direction of forward advancement of the piston (toward the needle), thereby advancing the piston within the container. The drive force may be exerted on the driven member by a spring, but also by a pressurized fluid, such as compressed air. For actuation of the drive unit, a blocking means, preventing advancement of the driven member, is released. Preferably, in some embodiments, the drive force is not exerted on the driven member before the release of the blocking means. According to the invention, the device comprises means for generating a controlled damping force, counteracting said drive force in the course of the piston being advanced, in addition to unavoidable counter forces. The unavoidable counter forces essentially are frictional forces acting on the piston when the piston is advanced and any forces generated by the work of displacement the piston performs. Since in addition to these unavoidable counter forces a damping force is generated which counters the drive force, the force difference acting on the driven member and resulting from the drive force, the unavoidable counter forces and the damping force can be controlled much more accurately than is the case in prior art devices.

The damping force is advantageously set to ensure that the product is administered with the most constant dispensing rate possible. In most applications, the dispensing rate is constant upon the piston being advanced at constant speed. Accordingly, the damping force in one embodiment is generated relative to or dependent on the advancing speed of the piston, preferably directly dependent on the advancing speed of the driven member. An acceleration increases the damping force and a deceleration decreases the damping force. If the advancing speed is kept constant, the damping force remains constant. Self-regulation is particularly preferred.

In preferred embodiments, the damping force will be reduced at least once during forward movement. Preferably, the damping force cycle exerted over the advance stroke of the piston is adapted to the cycle of the drive force exerted by the drive element. When the energy of the drive element decreases, the damping force decreases.

In one variation, the damping force is generated by the fact that a volume change work must be performed for the advancement of the piston, due to a chamber increasing or decreasing in volume upon the piston being advanced, with pressure compensation in the chamber only taking place at a delayed rate. This system is self-regulatory since change in speed brings about a corresponding change in the damping force.

In another variation, the damping force itself is a frictional force. Due to the design of the components being in frictional engagement for this purpose, the damping force, in this case caused by friction, is controlled.

The invention is preferably used in injection devices. However, it is not limited to this application. In principle, it may be profitably used in all devices for administering products in which a drive force causes advancement of a driven member, including such devices wherein the drive force directly causes movement of the drive member, and/or in which the advancement of a piston results from the interaction of a drive force with unavoidable counter forces which are predetermined within or result from manufacturing tolerances.

Another object of the invention is to improve removal of a needle safety cap typically applied to the needle in injection devices, in which the needle is surrounded by a needle safety sleeve during transport of the device and only projects over or from a front end of the needle safety sleeve during an injection. In prior art devices of this type, in particular semi-automatic injection devices and fully-automatic injection devices, so-called auto-injectors, the needle safety sleeve is slotted in order to allow the user to remove the needle safety cap by access through the slot. However, this means that the needle is visible in the transport position of the device and, in particular, when inserting the needle, thus possibly producing in the user a psychological barrier against insertion of the needle.

The present invention in large part solves this problem by connecting a stripper to the device in such a way that the stripper is displaceable against the direction of advancement when inserting the needle. Once the stripper has fulfilled its function, i.e. stripped the needle safety cap from the needle, thus allowing simple, complete removal of the cap from the device, the stripper according to the invention does not impede injection, although it is still connected to the device, due to the stripper being either shifted into or over the needle safety sleeve when the needle is being inserted. The needle then also projects over or beyond a front end of the stripper. The stripper is provided with engaging means for clamping or gripping the needle safety cap, but which do not impede forward movement of the needle in relation to the stripper and the needle safety sleeve after the needle safety cap has been removed.

It is another object of the invention to provide a device according to the invention, which can be safely handled after administration of a product, as a uncovered projecting needle poses a safety problem after administration of a product dose. This object is addressed by the invention in that a needle safety sleeve connected to the device, displaceable in and against the direction of needle advancement, is blockable against retraction from a base position in which it surrounds the needle beyond its tip as a protection. Preferably blocking is effected by providing a blocking element or, in a solution that is preferred, by automatic retraction of the inserted needle after or injection.

An advantage of the present invention is the operational safety is enhanced. In a device according to the invention, particularly in an auto-injection device in which the needle is automatically advanced by advancement of the container in relation to the base section, the container is advanced against an elastic restoring force, returning the container for replacement into its rear position.

This advantage is based on the knowledge that when the needle safety cap covering the needle is retracted, the container is pulled slightly forward against said elastic restoring force, followed by rapidly and abruptly bouncing back into its rear position immediately after the cap has been pulled off due to the restoring force. The container can thereby be damaged. Operational safety is not only jeopardized by the risk of damage to the container, but also by any splinters possibly breaking off from the container which may block an advancement of the container required for inserting the needle. This risk is prevented according to the invention by releasably locking or blocking the container in its rear position, i.e., the base position prior to inserting the needle, against unintentional forward movement.

In one preferred variation of this embodiment, the same blocking element which is already used for blocking the displaceable needle safety sleeve, as described above, is also used for blocking the container against forward movement, i.e., the same blocking element may be optionally used for the two blocking functions described.

The stripper, the blocking of the needle safety sleeve and the blocking of the container may advantageously be used in connection with controlled damping, but may also be applied individually and in a suitable combination with each other.

Other objects, features and advantages of the device and method of the present invention will become more fully apparent and understood with reference to the following description and appended drawings and claims.

BRIEF DESCRIPTION OF THE DRAWINGS

FIG. 1 depicts one embodiment of a device according to the present invention, and FIGS. 1a and 1b, taken from FIG. 1, depict details thereof;

FIG. 3 depicts another embodiment of a device according to the invention,

FIG. 3a depicts details of the embodiment shown in FIG. 3,

FIG. 4a-e depicts an auto-injection embodiment including blocking of the needle safety sleeve, FIG. 5a-e depicts the auto-injection device in accordance with FIG. 4a-e including blocking of the container.

DETAILED DESCRIPTION

Figure 2A:
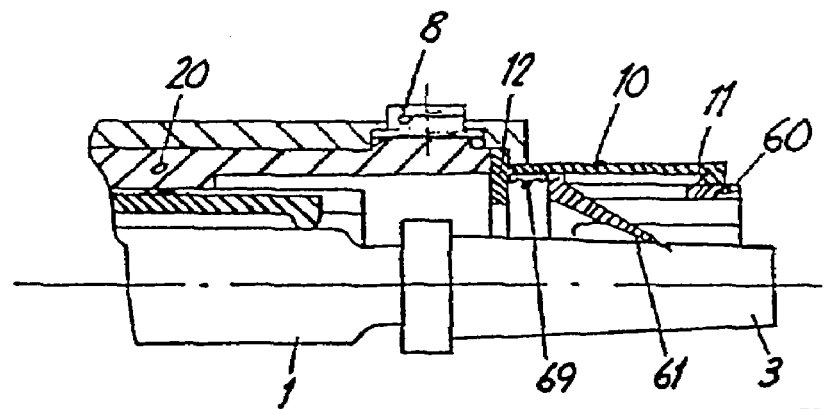
FIG. 2a depicts the stripper shown in FIG. 1 in a rear position.

The accompanying Figures and this description depict and describe embodiments of the injection device and method of the present invention, and features and components thereof. With regard to means for fastening, mounting, attaching or connecting the components of the present invention to form the device as a whole, unless specifically described otherwise, such means are intended to encompass conventional fasteners such as threaded connectors, snap rings, clamps such as screw clamps and the like, rivets, toggles, pins and the like. Components may also be connected by adhesives, glues, welding, ultrasonic welding, and friction fitting or deformation, if appropriate. Unless specifically otherwise disclosed or taught, materials for making components of the present invention may be selected from appropriate materials such as metal, metallic alloys, natural and manmade fibers, vinyls, plastics and the like, and appropriate manufacturing or production methods including casting, extruding, molding and machining may be used.

Any references to front and back, right and left, top and bottom and upper and lower are intended for convenience of description, not to limit the present invention or its components to any one positional or spacial orientation.

FIG. 1 is a longitudinal section of an injection pen, comprising an elongated, hollow cylindrical housing as a base section. The housing comprises a rear housing sleeve 4 being provided with an internal thread in a front section, and a front housing sleeve 7 being provided with an external thread in a rear section. The two housing sleeves 4 and 7 are screwed to each other in the sections of the two threads. A container 1 is arranged within the area of the front housing sleeve 7 and filled with an injectable product, in particular a fluid medicament.

The container 1 is an ampoule, common to such injection pens, including a piston 2 arranged in the same. By advancing the piston 2 towards an outlet at a front end of the container 1, a product dose is displaced from the container 1. An injection needle N is arranged on the container outlet pointing in the direction of advancement of the piston 2. The needle N is covered by a needle safety cap 3.

The container 1 is arranged in and centered by a container holder 30. The container holder 30, too, is formed by a sleeve and comprises in a front area three centering tongues 31 for centering the container 1. Further tongues 32 are formed evenly distributed over the circumference of the container holder 30 between the centering tongues 31 and projecting over the front ends of the centering tongues 31. The further tongues 32 act as stops when pushing back the needle safety sleeve 10.

An intermediate sleeve 20 is arranged in an annular gap between the container holder 30 and the front housing sleeve 7. The rear circumference of said intermediate sleeve 20 is provided with recesses through which the container holder 30 projects. Thereby, the container holder 30 is connected to the front housing sleeve 7 non-shiftably in relation to the front housing sleeve 7; in embodiment, the container holder 30 is screwed to the front housing sleeve 7. In contrast, the intermediate sleeve 20 is displaceable in relation to the front housing sleeve 7 and the container holder 30 after release of a blocking means 21, against the forward direction of the piston.

A releasing sleeve 35 is arranged in the rear housing sleeve 4, a front face of which is in contact with a rear face of the intermediate sleeve 20. The releasing sleeve 35 is essentially a hollow cylinder. A piston rod, extending rearwards from the piston 2, projects through it. The releasing sleeve 35 is arranged in the rear housing sleeve 4 and longitudinally displaceable in either direction. It is driven by a restoring spring 9 into its frontal position, as shown in FIG. 1, in which it is positioned flush in contact with a rear face of the intermediate sleeve 20 and a rear flange face of the container 1. A rear face 36 of the releasing sleeve 35 is chamfered outwards from a rear edge of an internal jacket face. When driving the releasing sleeve 35 back, said chamfered face 36 releases a drive unit for advancement of the piston 2 and dispensing the product.

The drive unit is formed by a driven member 40 and a drive spring acting as a drive element 49, clamped between the driven member 40 and the rear housing sleeve 4. The driven member 40 is pot-shaped, comprising a sleeve body open at its rear, formed by a simple circular cylindrical sleeve, projecting backwards from a closed sleeve bottom 41. Said sleeve body is arranged in a surrounding internal sleeve 5 of the rear housing sleeve 4, projecting forward from a rear face of the rear housing sleeve 4. The internal sleeve 5 forms a slideway for the driven member 40. In addition, it retains the driven member 40 against the force of the drive element 49 by a number of snap-on elements 6 being evenly distributed over a frontal circumference of the internal sleeve 5 (only one such element 6 is visible in the sectional view of FIG. 1) and surrounding a front face of the driven member 40.

FIG. 1 shows the injection device in its base position prior to injection, in which the driven member 40 is blocked by means of the snap-on elements 6 and the needle N is surrounded by the needle safety sleeve 10. Due to the needle N being surrounded by the needle safety sleeve 10, the needle is covered for the user of the injection device, in particular when being inserted into the skin, thus reducing a psychological block against inserting the needle N into one's own skin.

For insertion, the needle safety sleeve 10, together with the intermediate sleeve 20 and the releasing sleeve 35, in relation to the housing sleeves 4 and 7 and the container holder 30 with the container 1, can be shifted back against the forward direction (i.e., away from the needle). Furthermore, a sleeve-shaped stripper 60 is supported by the needle safety sleeve 10. Said stripper 60 projects over a front face of the needle safety sleeve 10 and can be shifted against a restoring element 69 provided in the needle safety sleeve 10, formed in the embodiment by a restoring spring, into the needle safety sleeve 10. The stripper 60 serves to strip off a needle safety cap, already removed in FIG. 1. Its removal function will be described with reference to FIGS. 2a and 2b.

For injecting the product the injection device is positioned on and pressed against the surface of a tissue, generally the human skin. This pressure initially pushes the stripper 60, forming the front end of the injection device, against the force of the restoring element 69, into the needle safety sleeve 10 up to a stop position, in which it is completely or almost completely surrounded by the needle safety sleeve 10. As soon as the stripper 60 has reached its stop position in the needle safety sleeve 10, the user releases the blocking means 21 by pressing the releasing button 8, thus releasing blocking against shifting of the intermediate sleeve 20 in relation to the front housing sleeve 7.

Since the injection device is still pressed against the tissue, the needle safety sleeve 10, and subject to the pressure exerted by the needle safety sleeve 10, the intermediate sleeve 20 and therefore the releasing sleeve 35, are pushed back within the housing. The needle N penetrates the tissue. Prior to injection, the needle safety sleeve 10 with a rear stop face, formed by an all-round shoulder 12 projecting inwards from a rear section of the needle safety sleeve 10, pushes against the tongues 32 of the container holder 30, acting as a stop, the chamfered face 36 of the releasing sleeve 35 engages the snap-on elements 6, and releases the fixation of the driven member 40 upon the sleeves 10, 20 and 35 being driven back further. Release of the fixation occurs at the point in time when the needle N has reached its desired predetermined penetration depth.

At this point in time, the driven member 40 is driven by the drive force of the drive element 49 in forward direction against a rear face of the piston rod and drives the piston 2 forward within the container while being driven forward itself. Pushing the piston 2 forward dispenses the product from the container through its outlet and the needle connected to it. In some embodiments, the full content of the container is dispensed upon the drive unit being released. In such embodiments, the content of the container is the product dose. In principle, however, by a constructive further development of the injection device, several selectable product doses could be dispensed during a plurality of injections.

During advancement of the driven member 40, the drive force stored in the drive element is gradually consumed when using a drive spring as a drive element 49, for instance, in accordance with the characteristics of the spring. The advance speed of the piston 2 would therefore decrease during the course of advancement and the dispensing rate would decrease. In order to compensate for the reduction in drive force while the piston 2 is being advanced, a pneumatic damping force acting on the drive member 40 is generated.

For this purpose, the driven member 40 and the housing, i.e., the rear housing sleeve 4 form walls of a low-pressure chamber K, the volume of which increases during advancement of the driven member 40. In this embodiment, the chamber K is formed by the sleeve bottom 41 and the sleeve body of the driven member 40 projecting from the same, and the rear face of the rear housing sleeve 4 and the internal sleeve 5 projecting from the same. The sleeve body of the drive member 40 and the internal sleeve 5 are displaced like telescopic sleeves in relation to each other. In the area of the slideways, i.e., between the external jacket face of the driven member 40 and the internal jacket face of the internal sleeve 5, a surrounding seal 42 is arranged. In the embodiment, a washer is placed in a circumferential groove of the sleeve body of the driven member 40.

Referring to FIG. 1, and FIGS. 1a and 1b, the rear face of the rear housing sleeve 4 comprises a passage "P" into which a seal 50, having a calibrated through-bore "T", but otherwise being airtight, has been inserted. Instead of a calibrated through-bore, a one-way or non-return valve "V" could be used, allowing the unimpeded escape of air upon the driven member 40 being driven back, but pressing against a valve seat on aspiration, this leaving only a defined, narrow through-bore, as predetermined in the design. The volume flow admitted per time unit into the chamber K is in any case less per time unit than the increase in volume of the chamber occurring during the advancement of the driven member 40, with a damping force therefore always being generated as long as the driven member 40 is advanced by the resulting drive force. The faster the driven member 40 is advanced the larger the generated damping force, i.e., the larger the effectively exerted drive force the larger the damping force generated. The type of damping force generation will therefore automatically compensate an energy consumption taking place in the drive unit, since with a decrease of the drive force a deceleration of the driven member 40 and a reduction of the damping force occurs. Simultaneously, other unavoidable or practically unavoidable counter forces are also compensated. Such superficial and other irregularities which cause deceleration or acceleration of the driven member 40, are automatically accompanied by a change in the volume change work to be performed by the drive element 49. An exemplary counter force is wall friction between the container 1 and the piston 2, which is not identical everywhere over the stroke of the piston 2 within the container 1. In addition, damping is further reduced due to the compressibility of the medium and the increase in chamber volume during the course of advancement of the driven member 40, thus compensating twice for energy consumption.

Figure 2B:
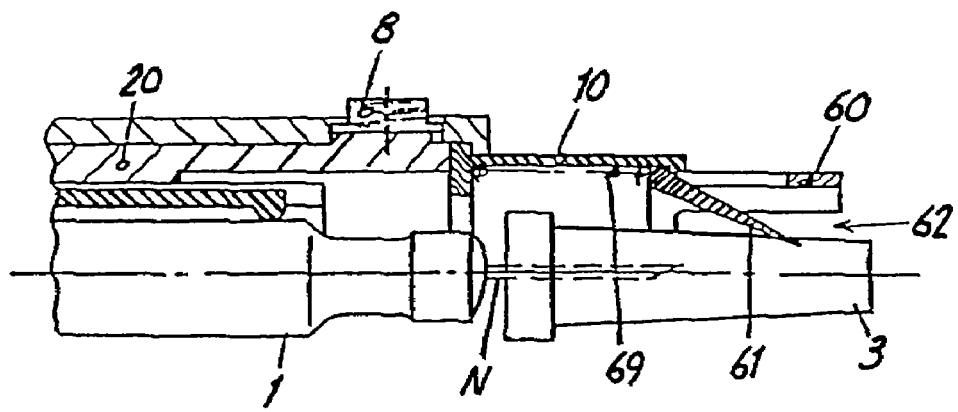
FIG. 2b depicts the stripper in a frontal position.

FIGS. 2a and 2b show how a needle safety cap 3 may be removed by means of the stripper 60. FIG. 2a shows the needle safety cap 3 completely covering or surrounding the injection needle. This corresponds to the state of the injection device directly after inserting the container 1 and screwing the two housing sleeves 4 and 7 together. At the same time, this represents the transport position of the injection device until just prior to injection. For preparation for an injection, the needle safety cap 3 is initially removed.

FIG. 2a shows how the removal of the needle safety cap 3 is initiated. For this, initially, the sleeve-shaped stripper 60 is pushed into the needle safety sleeve 10 against the pressure of the restoring element 69 until it presses against the needle safety cap 3 with two diametrically opposed engaging elements 61. The two engaging elements 61 project obliquely inwards, like barbs, from the rear interior jacket face of the stripper. When pushing back the stripper 60, the engaging elements 61 are more and more strongly pressed against the needle safety cap 3 which is widened towards the rear.

After firmly clamping the needle safety cap 3 between the engaging elements 61, the stripper 60 may be released. It is returned by the restoring element 69 to its frontal position, as shown in FIG. 2b, pushing it against a stop shoulder 11 of the needle safety sleeve 10, thus stripping the needle safety cap 3 from the container 1. In this position, the needle safety cap 3, which now only loosely covers the needle N, may be easily and completely removed manually from the front. In order to simplify manual removal, the stripper 60 is provided with at least two gripping recesses 62.

As the stripper 60 is permanently attached to the injection device, the user does not have to first tediously introduce it for removal of the needle safety cap 3. On the other hand, it does not interfere in any way during injection. Another advantage resides in the fact that the needle safety sleeve 10 can be designed completely closed, i.e., without any gripping slot for removal of the needle safety cap 3, thus allowing the needle N to be completely covered.

FIG. 3 shows an auto-injection device not only for automatically dispensing the product but also for automatically inserting the needle. Where the same references are used in FIG. 3 as in the embodiments described above, components of a substantially identical function are identified. As to the basic mode of operation of the auto-injection device, reference is made to the applicant's parallel German patent application No. 198 22 031 and the corresponding U.S. application Ser. No. 09/311,435, the disclosures of which are incorporated herein by reference:

In contrast to the embodiment of FIG. 1, FIG. 3 depicts an exemplary embodiment of a damping mechanism in an auto-injection device wherein damping of the drive force exerted on the driven member 40 is effected by friction. This damping frictional force is exerted between a contact pressure element 45, designed as a pliable ring, clamped between the sleeve-shaped driven member 40 and a transfer member 46, which is also sleeve-shaped and surrounds the driven member 40 during advancement. This damping frictional force is exerted between a contact pressure element 45, designed as a pliable ring, clamped between the sleeve-shaped driven member 40 and a transfer member 46 which is also sleeve-shaped and surrounds the driven member 40 during advancement.

In the auto-injection device of FIG. 3, the injection cycle is essentially as follows: a blocking unit blocking the advancement of the driven member 40 is released by pressing a release tongue 8, and the driven member 40 is driven forward to the left in FIG. 3, by the drive force of the drive element 49, which is also a compression spring in this embodiment. Initially, the contact pressure element 45 forms a coupling between the driven member 40 and the transfer member 46, as shown specifically in detail in FIG. 3a. The driven member 40 drives the transfer member 46 via this coupling The transfer member 46, in turn, advances the container 1, including the needle N attached to the same at the front end, in relation to the housing.

Thereby, the needle N is pushed forward out of the needle safety sleeve 10a and is inserted. The needle safety sleeve 10a, in this embodiment, is firmly attached to the housing. Insertion is limited by stopping of the container holder 30 at the housing. When stopped, the coupling between the driven member 40 and the transfer member 46 is released, as clearly shown in FIG. 3a. During further advancement, the driven member 40 is driven forward in relation to the transfer member 46, presses against the piston rod and advances by its own further advancement the piston 2 in the container 1, thus allowing the product to be dispensed.

The contact pressure element 45 is a slotted spring washer similar to a piston ring. This washer is placed in an all-round groove 44 on an external circumference of the driven member 40, pressing elastically and radially against the driven member and the internal jacket slideway 43 of the transfer member 46, i.e., a type of counter element. The external circumference of the driven member 40 or the internal jacket slideway 43 of transfer member 46 may provide a contact pressure surface for contact pressure element 45. The wall frictional force exerted between the contact pressure element 45 and the transfer member 46 decreases during the course of advancement of the driven member 40 due to the internal jacket slideway 43 of the transfer member 46 being widened in the forward direction. This compensates for a decrease of the drive force of the drive element 49.

A guide ring 47 is placed in a rear section of the transfer member 46, serving as a straight guide for the driven member 40. Said guide ring 47 may also be formed as a sealring comprising one or several calibrated through-bores or a non-return valve in accordance with the embodiment of FIG. 1. In this way a pneumatic damping force instead of or in addition to the frictional damping force could be generated. In such an embodiment, the low-pressure chamber would be formed in the gap section between the transfer member 46 and the driven member 40 being shifted into the transfer member 46.

A tensioning handle 8a, projecting through the housing 4, is used for returning into rear position and tensioning a holding 4a and release sleeve 4b together with the driven member 40, the holding 4a and release sleeve 4b being displaceably arranged in the housing and jointly connected with the driven member 40.

FIGS. 4a-e and 5a-e, which include elevational, sectional and cross-sectional views, show an auto-injection device in which the advancement of the container 1 for inserting the needle is effected in the conventional way by the piston 2, in contrast to the device of FIG. 3, i.e. advancement of the container 1 is not decoupled from the advancement of the piston 2, but is rather effected by the piston 2. However, the injection device of FIGS. 4a-e and 5a-e, like that shown in FIG. 1, comprises a needle safety sleeve 10, displaceable in either longitudinal direction in relation to the housing. This displaceable needle safety sleeve 10 covers the needle after injection, i.e. after retraction, which is not possible in the auto-injection device depicted in FIG. 3.

In contrast to the embodiment of FIG. 1, however, a stripper 65 is provided, not permanently connected to the injection device, but which must be inserted between the needle safety cap 3 and the needle safety sleeve 10 for removing the needle safety cap 3 until it grips behind the needle safety cap 3 like a claw, thus allowing removal of the needle safety cap 3 together with the stripper 65.

FIG. 4a-e shows an injection device after injection and retraction of the needle with the needle safety cap 3 already inserted on it for future transport. A special feature of this embodiment is the blocking of the needle safety sleeve 10.

Blocking of the needle safety sleeve 10 securely ensures that the tip of the needle cannot freely project, thus eliminating any risk of damage to the needle N and in particular injury. The needle safety sleeve 10 is blocked by a blocking element 80 relative to the housing in such a way as to prevent the needle safety sleeve 10 being pushed back against forward direction.

The blocking element 80 is formed by means of a ring section comprising two engaging elements 81, having the shape of two webs, projecting from an inner jacket face of said ring. As best shown in FIG. 5a-e on the bottom left-hand side, the needle safety sleeve 10 comprises two slots 15 gripped by one each of the engaging elements 81 upon the blocking element 80 being placed on the housing. The engaging elements 81 then form stops for those walls of the slots 15 which extend in circumferential direction. The blocking element 80 is obtained by cutting a sleeve open, which sleeve is a circular annular sleeve in the embodiment, wherein cutting open occurs in longitudinal direction and outside of the central longitudinal axis of the sleeve, so that the blocking element 80 comprises a shell which when seen in cross-section, projects a little over the semicircle. Thus, the blocking element 80 as explained hereafter with reference to FIG. 4a-e, is insertable over the rear housing sleeve 4 and projects over the largest diameter of the rear housing sleeve 4 when inserted over it.

As best shown in cross-sections B-B and C-C of FIG. 4a-e, the blocking element 80 in carrying out its function as a block is retained on the needle safety sleeve 10 by means of its snap-in connection. For this the engaging elements 81 are designed flexibly and elastically and provided with snap-in projections at the front, gripping one of the internal slot edges after passing through each slot 15, thus retaining the blocking element 80 like a snapper in blocked position, but allowing easy removal when required.

FIG. 5a-e shows the blocking element 80 in its second function, in which it blocks the container 1 against advancement. Without this blocking, during removal of the needle safety cap 3, the container 1 would be carried along in forward direction over a certain distance against the force of the elastic restoring element 29 and would snap back into its rear position depicted in FIG. 5a-e the moment the needle safety cap 3 is removed, due to the force of the restoring element 49. When snapping back, there would be a risk of damaging the container and an ensuing risk of possibly blocking forward movement of the container 1 when inserting the needle N.

In order to prevent this, the blocking element 80 is attached to a section of the housing covering the rear edge of the container 1 while the injection device is in its transport position until the needle safety cap 3 is removed. In this position, as shown in the longitudinal section of FIG. 5a-e, the shell body of the blocking element 80 closely surrounds the housing, as shown in particular in cross-section E-E, and is retained to the rear housing sleeve 4 due to its ends projecting over the semicircle. The engaging elements 81 do not assume any retention function for the blocking element 80, but now serve as a block for the container 1. For this purpose, the engaging elements 81 grip through the housing and are positioned in front of an all-round flange provided at the rear end of the container 1 upon the blocking element 80 being attached. Since this rear flange of the container 1, extending radially outwards, pushes against the engaging elements 81 of the blocking element 80 when removing the needle safety cap 3, the container 1 is blocked in rear position and cannot therefore be advanced.

In its position shown in FIG. 5a-e, the blocking element 80 fulfills a third function, namely to prevent release of the drive unit by blocking the movement of a release means 70. The release means 70 is then able to release the driven member 40 from its blocked position when the blocking element 80 is removed from the housing, thus only allowing advancement of the release means 70 in relation to the housing at this point.

Figure 6A:
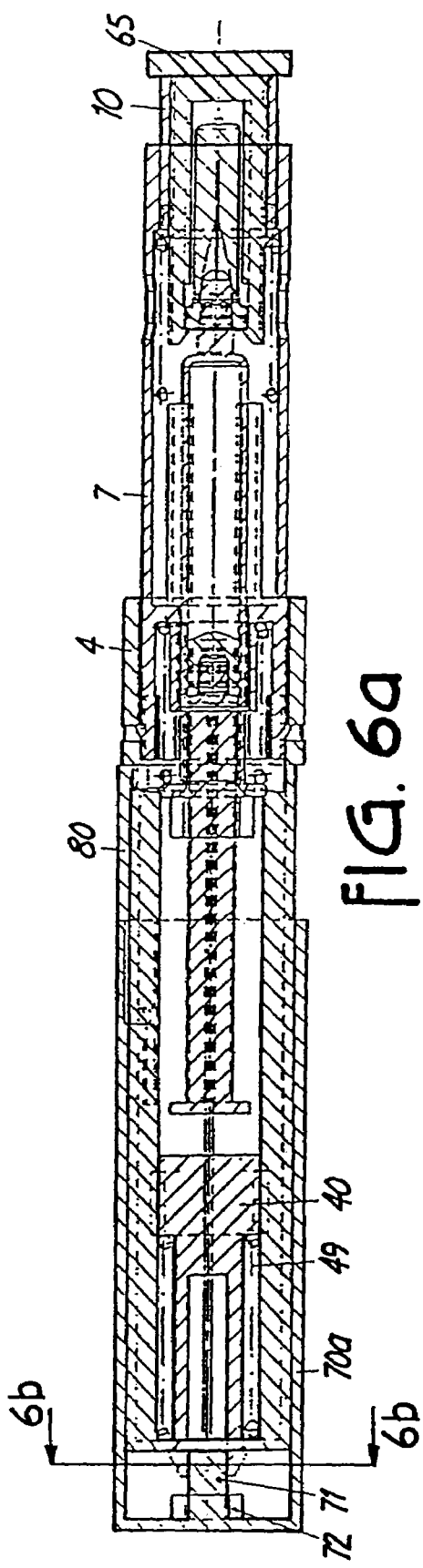
FIG. 6a-b depicts the auto-injection device in accordance with FIGS. 4a-e and 5a-e comprising an alternative release means.
Figure 6B:
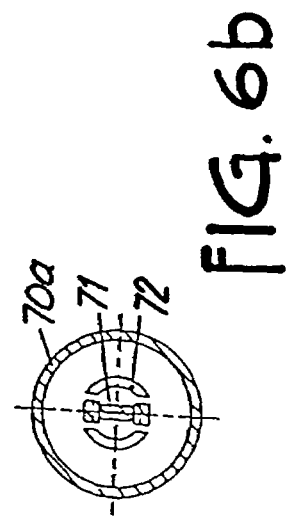

FIG. 6*a-b* shows an auto-injection device which corresponds to the injection device of FIGS. 4*a-e* and 5*a-e*, except for the release means 70 for the driven member 40. A release means 70*a* of FIG. 6*a-b*, too, consists of a sleeve-shaped body comprising a rear sleeve bottom. The driven member 40 is both blocked in its rear position by the release means 70*a* and released when operating the release means 70*a* accordingly.

The rear end of the driven member 40 ends in snap means, projecting through a rear face wall of the housing and surrounding its rear circumferential edge, with the snap means of the driven member 40 being pushed outwards due to their inherent elasticity and retained in their positions. As an additional security against unintentional disengagement, for instance due to impact, a blocking part 71 of the release means 70*a*, which projects from its sleeve bottom and is formed as a small rectangle when seen in cross section, engages with its long side between two diametrically opposed snap means of the driven member 40. In this rotational position, it prevents both snap means bending towards each other in the position of the release means 70*a* shown in FIG. 6*a-b*, which would release the snap-in connection. Furthermore, two contact pressure members 72 are projecting from the sleeve bottom of the release means 70*a* at a distance from both sides of the blocking part 71, which when seen in cross section have the shape of circular segments. The blocking part 71 projects over the contact pressure members 72. The blocking element 80 is initially removed for release of the driven member 40, followed by rotating the release means 70*a* at least so far around its longitudinal axis that the snap means of the driven member 40 can be bent towards each other. During rotation of the release means 70*a*, the contact pressure members 72 are positioned over the snap means of the driven member 40 when seen in cross section. When pushing the release means 70*a* towards the driven member 40, the impression elements 72 push against the snap means of the driven member 40, which comprise chamfered rear faces, thus allowing them to bend towards each other under the pressure of the impression members 72, thereby releasing the snap-in connection of the driven member 40 with the housing. Due to the pressure exerted by the drive unit 49 the driven member 40 is then driven forward.

The blocking element 80 may be designed as a rotary element instead of a plug-in element and could, therefore, remain on the housing after blocking of the container has been released.

Figure 7A:
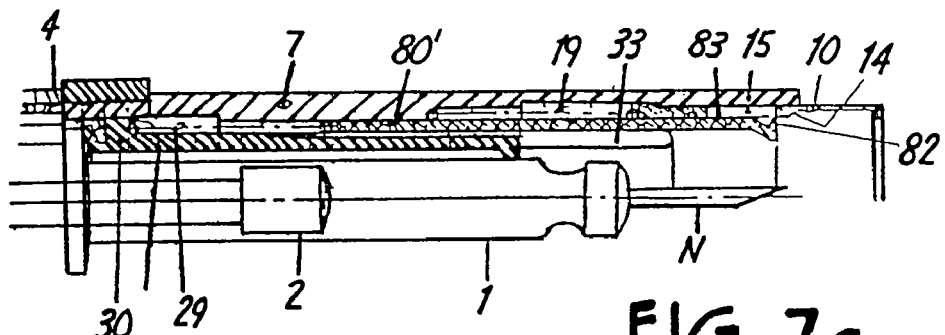
FIG. 7a-c depicts an auto-injection device also including blocking of the needle safety sleeve.
Figure 7B:
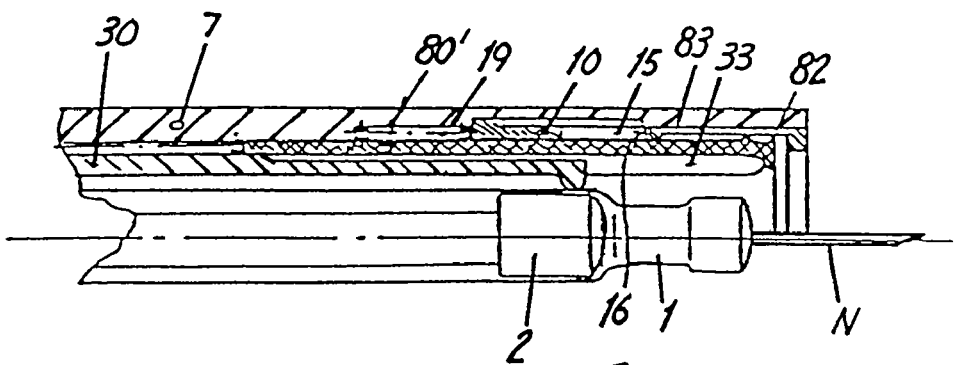
Figure 7C:
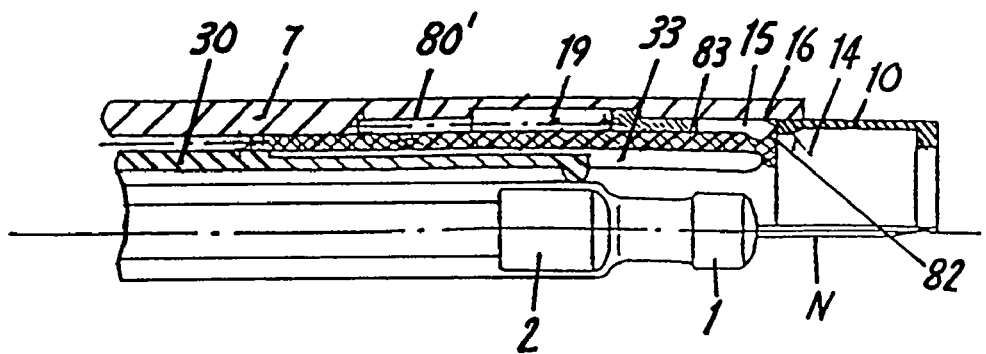

FIGS. 7*a*, 7*b* and 7*c* show the mode of operation of the needle protection apparatus which prevents the needle N from freely projecting from the housing after retraction from the tissue when it could be broken and/or cause injury if not handled carefully. A feature of the needle protection apparatus is that the needle safety sleeve 10, which is displaceable in relation to the housing for the purpose of insertion, is blocked in a needle protection position after retraction of the needle, so that it can no longer be pushed into the housing. Pushing over the housing externally would also be feasible. The mode of operation of the pen for inserting the needle N and dispensing the product corresponds to that of the pen shown in FIG. 3.

FIG. 7*a* shows the front section of the pen in its base position directly before injection. FIG. 7*b* shows the pen in the frontal position of the container 1, i.e. in injecting position. The needle safety sleeve 10 has been pushed against the force of the restoring element 19 into its most rear displacement position in relation to the housing sleeve 7. The needle N projects out of the housing and the needle safety sleeve 10 by the desired length.

The needle safety sleeve 10 comprises a rear stop face and a front stop face, limiting the displacement path of the needle safety sleeve 10 in relation to the front housing sleeve 7 in and against forward direction. When moving the needle safety sleeve 10 in either direction, it passes over a blocking sleeve 80' provided in the housing and secured against displacement and preferably also rotation, said blocking sleeve 80' comprising at its front end at least one hook 82 which is chamfered outward obliquely or curved. In an internal jacket section, with which it slides over the hook 82, the needle safety sleeve 10 comprises a widened section, extending approximately over the length of its maximum displacement path, the widened section being preferably a slightly widened internal diameter. A transitional section 14 extending between the widened section and the adjacent internal cross section is chamfered, thus enabling the needle safety sleeve 10 to slide over the hook 82, subject to the pressure of the restoring element 19, up to a point behind the transitional area 14. Behind the transitional area 14, in a central section the needle safety sleeve 10 is provided with longitudinal slots 15, the front faces 16 of which, as best shown in FIG. 7*c*, form stop faces each for one of the hooks 82.

The blocking sleeve 80' ends in a number of elastic and flexible tongues 83, evenly distributed over the circumference of the sleeve, the free front ends of which are each formed as a hook 82. The container holder 30 also ends in tongues 33 towards its free front end. When advancing the container holder 30 against the force of the restoring element 29, these tongues 33 are positioned below the tongues 83 of the blocking sleeve 80'. Each of the tongues 83 is thus supported radially towards the inside and can no longer be bent radially inward when the container is in its frontal position. The tongues 83 are not only supported by the tongues 33 but are in addition pushed radially outwardly. In comparison with the tongues 83, the tongues 33 are rigidly formed and may be more rigid than tongues 83.

After retraction of the needle N, the needle safety sleeve 10 is pushed forward again by the restoring element 19. Due to the chamfered face 14 and/or the chamfered shape of the at least one hook 82, the needle safety sleeve 10 is pushed over said hook 82, the end tip of which is, furthermore, elastic and flexible. However, as soon as the needle safety sleeve 10 has been advanced again to a point at which its stop face 16 is positioned in front of the hook 82, when seen in forward direction, it is blocked against return by the hook 82 positioned against the stop face 16 in stop position. The hook 82 and the needle safety sleeve 10 are in contact with each other by their stop faces which point vertically to the direction of displacement. In its safety position shown in FIG. 7*c*, the needle N is protected after injection by means of the needle safety sleeve 10.

The container holder 30 is therefore simultaneously used as a displaceable support for the at least one hook 82 and fulfills, according to the invention, the dual function of retaining the container 1 and blocking the needle safety sleeve 10. The needle safety apparatus does not require the auto-injection device to be designed according to the invention, although it is used most preferably in combination with the same. It may also be used to advantage in generic auto-injection devices.

The foregoing description of embodiments of the invention has been presented for the purpose of illustration and description. It is not intended to be exhaustive or to limit the invention to any precise form disclosed. The above described embodiments were chosen and described to provide an illustration of the principles of the invention and its practical application, and to enable one of ordinary skill in the art to utilize the invention in various embodiments and with various modifications as are suited to the particular use contemplated. All such modifications and variations are within the scope of the invention as determined by the appended claims when the claims are interpreted in accordance with the breadth to which they are fairly, legally, and equitably entitled.

What is claimed is:

1. A device for administering an injectable product, comprising:
   a) a base section;
   b) a container arranged in the base section, the container being displaceable in relation to said base section from a base position to an injecting position, wherein when the container is in the injecting position, a product dose is dispensed from the container through a needle by displacement of a piston associated with the container; and
   c) a drive unit, comprising a driven member and a drive element, the drive element applying a drive force on said driven member upon actuating the drive unit, by which drive force said driven member is displaced in the direction of the piston and the container is moved from the base position to the injecting position, wherein
   d) a damping force interacts with the drive force and changes during displacement of the driven member.

2. The device according to claim 1, said damping force generated by contact between said driven member and a counter element, wherein one of said driven member and said counter element provides a contact pressure surface.

3. The device according to claim 2, wherein said contact pressure surface is adapted to cause the damping force to decrease in the course of displacement of the driven member.

4. The device according to claim 1, said damping force generated relative to said driven member and a counter element, wherein one of said driven member and said counter element provides a contact pressure surface.

5. The device according to claim 4, further comprising a contact pressure element arranged between said driven member and said counter element.

6. The device according to claim 5, wherein the contact pressure element comprises a pliable ring.

7. A device for administering an injectable product, comprising:
   a base section;
   a container arranged in the base section, the container being displaceable in relation to said base section from a base position to an injecting position, wherein when the container is in the injecting position, a product dose is dispensed from the container by displacement of a piston associated with the container; and
   a drive unit comprising a driven member and a drive element, the drive element applying a drive force on said driven member upon actuation of the drive unit, by which drive force said driven member is displaced generally longitudinally in the direction of the piston to move the container from the base position to the injecting position and to advance said piston within said container; wherein
   a damping force interacts with the drive force, said damping force produced by a contact pressure element generally between said driven member and a counter element so as to cause the damping force to decrease during the displacement of the driven member.

8. The device according to claim 7, the contact pressure element is generally between said driven member and a counter element and associated with one of said driven member and counter element so as to cause the damping force to decrease during the displacement of the driven member.

9. The device according to claim 7, wherein the contact pressure element comprises a guide ring.

10. The device according to claim 7, wherein the damping force decreases during displacement of the driven member by the counter element.

11. A device for administering an injectable product, comprising:
    a base section;
    a container arranged in the base section, the container being displaceable in relation to said base section from a base position to an injecting position, wherein when the container is in the injecting position, a product dose is dispensed from the container by displacement of a piston associated with the container; and
    a drive unit comprising a driven member and a drive element, the drive element applying a drive force on said driven member upon actuation of the drive unit, by which drive force said driven member is displaced generally longitudinally in the direction of the piston to move the container from the base position to the injecting position and to advance said piston within said container; wherein
    a frictional damping force interacts with the drive force, said frictional damping force produced by a compressing of the driven member over a portion of the length of the driven member, the compressing of the driven member decreasing during the displacement of the driven member.

12. A device for administering an injectable product, comprising:
    a) a base section;
    b) a container arranged in the base section, the container being displaceable in relation to said base section from a base position to an injecting position, wherein when the container is in the injecting position, a product dose is dispensed from the container through a needle by displacement of a piston associated with the container; and
    c) a drive unit, comprising a driven member and a drive element, the drive element applying a drive force on said driven member upon actuating the drive unit, by which drive force said driven member is displaced in the direction of the piston to move the container from the base position to the injecting position and to advance said piston within said container; and
    d) a damping mechanism operably associated with the drive unit for generating a damping force, said damping force decreasing during displacement of the driven member and produced by an elastic pressing.

13. The device according to claim 12, said damping force decreasing during displacement of the driven member and produced by an elastic pressing between the driven member and a counter element.

14. The device according to claim 12, said damping force produced by an elastic pressing between said driven member and a counter element.

15. A device for administering an injectable product, comprising:
 a) a base section;
 b) a container arranged in the base section comprising a piston, the container being displaceable in relation to said base section from a base position to an injecting position, and the piston being displaceable upon the container reaching the injecting position; and
 c) a drive unit, comprising a driven member and a drive element, the drive element applying a drive force on said driven member upon actuating the drive unit, by which drive force said driven member is displaced to cause said container to move from the base position to the injecting position, wherein upon reaching the injecting position, the piston is displaced to cause a product dose to be dispensed from the container; wherein,
 d) a damping force interacts with the drive force and changes during displacement of the driven member.

16. The device of claim 15, wherein the piston is spaced from the drive unit.

17. The device of claim 15, wherein the piston is coupled to the drive unit after the container reaches the injecting position.

18. The device of claim 15, wherein the piston is coupled to the drive unit when the container is in the base position.

19. A method for injecting an injectable product, comprising:
 providing an injection device comprising:
 a) a base section;
 b) a container arranged in the base section, the container being displaceable in relation to said base section from a base position to an injecting position, wherein when the container is in the injecting position, a product dose is dispensed from the container through a needle by displacement of a piston associated with the container; and
 c) a drive unit, comprising a driven member and a drive element, the drive element applying a drive force on said driven member upon actuating the drive unit, by which drive force said driven member is displaced in the direction of the piston and the container is moved from the base position to the injecting position, wherein
 d) a damping force interacts with the drive force and changes during displacement of the driven member; and
 causing the drive force of the drive unit to initiate.

20. A device for administering an injectable product, comprising:
 a base section;
 a container arranged in the base section, the container being displaceable in relation to said base section from a base position to an injecting position, wherein when the container is in the injecting position, a product dose is dispensed from the container by displacement of a piston associated with the container; and
 a drive unit comprising a driven member and a drive element, the drive element applying a drive force on said driven member upon actuation of the drive unit, by which drive force said driven member is displaced generally longitudinally in the direction of the piston to move the container from the base position to the injecting position and to advance said piston within said container; wherein
 a damping force is generated during operation of the administering device, said damping force comprising an elastic pressing of said driven member, said elastic pressing taking place over a portion of the length of said driven member and changes during displacement of the driven member.

21. The device according to claim 20, wherein the elastic pressing comprises radial pressing.

* * * * *

UNITED STATES PATENT AND TRADEMARK OFFICE
CERTIFICATE OF CORRECTION

PATENT NO. : 7,357,791 B2  
APPLICATION NO. : 11/554308  
DATED : April 15, 2008  
INVENTOR(S) : Fritz Kirchhofer et al.

Page 1 of 1

It is certified that error appears in the above-identified patent and that said Letters Patent is hereby corrected as shown below:

SPECIFICATION

Certificate of Letters Patent

| Column | Line | Delete | Correction |
|---|---|---|---|
| 8 | 45-50 | "This damping frictional force is exerted between a contact pressure element 45, designed as a pliable ring, clamped between the sleeve-shaped driven member 41 and a transfer member 46 which is also sleeve-shaped and surrounds the driven member 40 during advancement." | Delete sentence as duplicative of previous sentence beginning in Column 8, Line 40 |

Signed and Sealed this

Sixteenth Day of September, 2008

JON W. DUDAS  
*Director of the United States Patent and Trademark Office*